US005095899A

United States Patent [19]

Green

[11] Patent Number: 5,095,899

[45] Date of Patent: Mar. 17, 1992

[54] AIR DELIVERY SYSTEM

[76] Inventor: Thomas G. Green, 15843 N. 4th Ave., Phoenix, Ariz. 85023

[21] Appl. No.: 439,825

[22] Filed: Nov. 21, 1989

[51] Int. Cl.[5] .................... A61M 16/00; A62B 7/00; A62B 9/02; A62B 18/02

[52] U.S. Cl. .................... 128/204.18; 128/202.13; 128/200.25; 128/205.25; 128/205.24

[58] Field of Search .................... 128/200.24, 200.25, 128/204.18, 202.27, 205.13, 205.18, 202.13, 205.25, 205.24

[56] References Cited

U.S. PATENT DOCUMENTS

| | | | |
|---|---|---|---|
| 386,751 | 7/1888 | Loomis | 239/270 |
| 441,119 | 11/1890 | Merryman | 128/200.25 |
| 667,840 | 2/1901 | Guthrie | 128/205.13 |
| 839,486 | 12/1906 | Lafave | 128/202.13 |
| 898,524 | 9/1908 | Sullivan | 128/200.25 |
| 916,886 | 3/1909 | Merryman | 128/200.25 |
| 958,427 | 5/1910 | Panian | 128/205.13 |
| 989,880 | 4/1911 | Shaw | 128/200.25 |
| 1,808,281 | 2/1930 | Balthazor | 239/270 |
| 2,120,563 | 6/1938 | Lamb | 98/1 |
| 2,299,793 | 10/1942 | Cannaday et al. | 128/140 |
| 2,515,578 | 7/1958 | Wilson et al. | 299/109 |
| 4,165,738 | 8/1979 | Graves et al. | 128/142.4 |
| 4,373,522 | 2/1983 | Zien | 128/206.12 |
| 4,440,164 | 4/1984 | Werjefelt | 128/205.25 |
| 4,467,796 | 8/1984 | Beagley | 128/202.13 |
| 4,974,584 | 12/1990 | Goodnoe | 128/202.13 |

FOREIGN PATENT DOCUMENTS

| | | | |
|---|---|---|---|
| 571422 | 8/1945 | United Kingdom | 239/270 |

*Primary Examiner*—Edgar S. Burr
*Assistant Examiner*—Kimberly L. Asher
*Attorney, Agent, or Firm*—Cahill, Sutton & Thomas

[57] ABSTRACT

The invention provides an air delivery system for emergency workers, wherein the air delivery system is adapted to be used with a water hose. The system includes a source of compressed air fluidically connected to the water hose to purge water from the water hose. Pressure adjusting means adjust the compressed air pressure to less than approximately 300 psig. Means are provided for further reducing the air pressure, after the water is purged, to a pressure in the range of approximately 8–50 psig. The system further includes means for transferring air from the air hose to a breathing cavity of the worker.

15 Claims, 3 Drawing Sheets

AIR DELIVERY SYSTEM

FIELD OF THE INVENTION

The invention relates generally to an air delivery system for use by emergency workers such as firemen who may be trapped inside a burning building.

DESCRIPTION OF THE PRIOR ART

Fires commonly produce toxic and lethal fumes in addition to smoke. Indeed, injuries and fatalities relating to these fires are often attributed to asphyxiation rather than burning. Therefore when firemen enter burning buildings, they generally carry on their backs a self-contained breathing apparatus such as a compressed air tank attached by a hose to a breathing mask. However, such tanks carry only approximately 30 minutes worth of air. In many fires, the floor or roof of a building may collapse, trapping a fireman. In such situations, the fireman has a high risk of suffocation because the time required to rescue the fireman may exceed the time available from the air tank.

Several prior art devices have attempted to address this problem. For example, U.S. Pat. No. 386,751 to Loomis discloses a device for supplying air to fireman in burning buildings in which the water hose carried by the fireman incorporates a separate air hose within it. The air and water is intended to be delivered simultaneously. U.S. Pat. No. 1,808,281 to Balthazor discloses a system wherein fresh air is drawn inwardly from the nozzle end of the hose by taking fresh air directly from the stream of water passing through the hose. Finally, U.S. Pat. No. 2,515,578 to Wilson discloses a system similar to that of Balthazor in that air is commingled with water flowing through the nozzle of the hose.

The references tabulated below disclose relatively complicated systems for providing fresh air to enclosed areas. None of these references pertain specifically to fire fighting situations.

| | INVENTOR |
|---|---|
| U.S. PAT. NO. | |
| 2,120,563 | Lamb |
| 2,299,793 | Cannaday, et al. |
| 4,165,738 | Graves |
| 4,373,522 | Zien |
| 4,440,164 | Werjefelt |
| 4,467,796 | Beagley |
| GREAT BRITAIN PATENT NO. | |
| 5,71,422 | |

Nothing in the prior art discloses an effective, rapid system for delivering air to a trapped fireman through the water hose carried by the fireman.

SUMMARY OF THE INVENTION

Briefly described and in accordance with one embodiment of the invention, the invention provides an air delivery system for emergency workers, wherein the air delivery system is adapted to be used with a water hose. The system includes a source of compressed air fluidically connected to the water hose to purge water from the water hose. Pressure adjusting means adjust the compressed air pressure to less than approximately 300 psig. Means are provided for further reducing the air pressure, after the water is purged, to a pressure in the range of approximately 8-50 psig. The system further includes means for transferring air from the air hose to a breathing cavity of the worker.

It is an object of the present invention to provide a safe, rapid and effective system for delivering air to emergency workers detained in areas where the supply of breathable air is limited.

It is another object of the present invention to deliver air to trapped firemen through the water hose conventionally carried by such firemen.

It is another object of the present invention to provide an uncomplicated and inexpensive system for delivering emergency air to firemen detained in burning buildings.

Other objects, advantages and features of the present invention will become apparent from the following specification when taken in conjunction with the accompanying drawings.

DESCRIPTION OF THE PREFERRED EMBODIMENT

Figure 1:
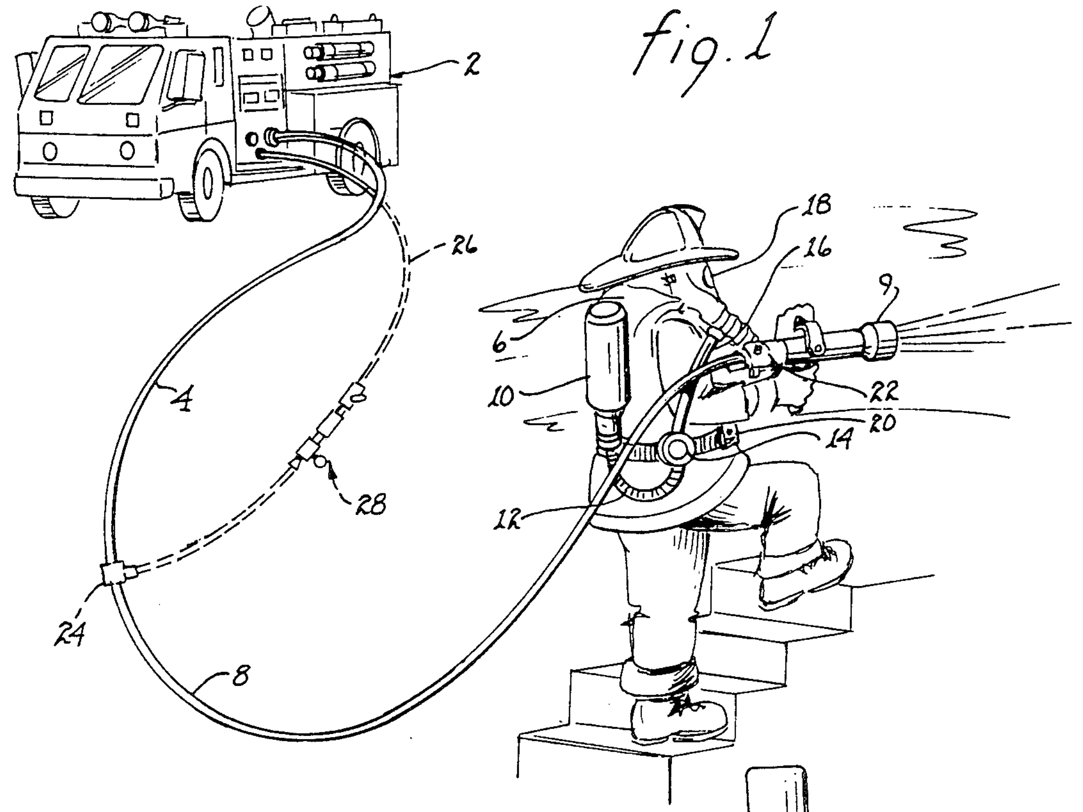
FIG. 1 is a perspective view of a fireman using conventional firefighting equipment, with elements of the present invention sketched in dashed lines for comparison.

FIG. 1 shows a fireman using conventional firefighting equipment. At the scene of a fire, pumper truck 2 provides water to douse the fire. A first hose 4, approximately 15-50 feet long, is quickly attached to the water reservoir in the truck. When a fireman 6 is ready to enter the burning building, an attack line 8 approximately 150 feet long is attached to first hose 4. First hose 4 and attack line 8 are of similar construction and have the same diameter, typically, $1\frac{1}{2}$, $1\frac{3}{4}$, 2 or $2\frac{1}{2}$ inches. First hose 4 and attack line 8 typically have a maximum pressure rating of 300 psig. Water flowing through the hoses is directed at the fire by nozzle 9.

To protect himself from smoke and toxic fumes, fireman 6 invariably wears emergency breathing apparatus consisting of compressed air tank 10 connected by tank hose 12 to a regulator 14 which controls the flow rate and pressure of air into mask hose 16 leading to breathing mask 18. Tank 10 generally contains only approximately 30 minutes worth of air; regulator 14 is worn on belt 20, so that the fireman can turn air flow on and off as conditions require, in order to conserve the air supply. Fireman 6 also usually carries a two-way radio to communicate with firemen outside the building.

In FIG. 1, elements comprising the air delivery system of the present invention are shown by dashed lines to illustrate how the present invention is integrated into conventional firefighting equipment. Air extractor 22 is connected to attack line 8 immediately behind nozzle 9.

Extractor 22 contains at least three quick-connect ports 23, each of which is adapted to connect to a mask hose 16. Extractor 22 will usually remain in place whether or not the air delivery system is being used. Air inductor 24 is attached to the hose line at the junction of first hose 4 and attack line 8. Extractor 22 and inductor 24 are constructed from aircraft aluminum pipe having a wall thickness of ½ inch; the extractor and inductor have diameters suitable for the various available hose diameters. That is, 1½, 1¾, and 2-inch hoses require a 1½ inch extractor and a 1½ inch inductor; a 2½ inch hose requires a 2½ inch extractor and a 2½ inch inductor. Attached to inductor 24 is check valve 25, to which is connected air brake line 26. Brake line 26 connects to the pumper truck's air brake air storage tank (not shown). The flow of air from truck 2 through air brake line 26 is regulated by a gauge and set of valves shown generally at reference numeral 28.

The air delivery system of the present invention is intended to be used only in an emergency such as when a fireman is delayed inside a burning building and wants to conserve the supply of air in tank 10; the system is not intended to replace the self-contained breathing apparatus conventionally worn by firemen. Typically, the air delivery system will be needed if part of a burning building collapses, temporarily trapping one or more firemen inside until rescue occurs. Because the air delivery system delivers air through the water hose, it is important that a fireman using the system not be immediately at risk from flames; when the air delivery system is in use, water to douse such flames will be temporarily unavailable.

Figure 6:
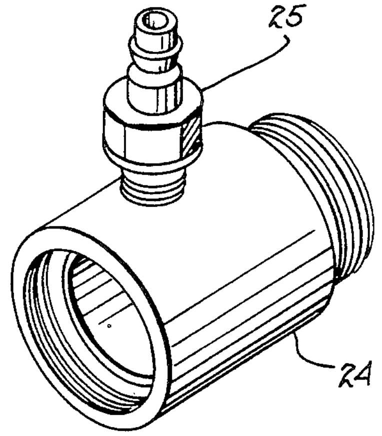
FIG. 6 is a closeup view of the air inductor of the present invention.

The air delivery system is put into operation as soon as fireman 6 inside a burning building uses his radio to signal a fireman outside the building that the air supply in tank 10 is running low. The outside fireman immediately attaches air inductor 24 to the junction of first hose 4 and attack line 8, and also connects air brake line 26 to check valve 25 and to the air brake air storage tank of truck 2. Air inductor 24 and check valve 25 are shown in greater detail in FIG. 6.

The outside fireman then opens main valve 30, resulting in delivery of air having a pressure of 120 psig at a rate of 15 cubic feet per minute. The air flows through air brake line 26, inductor 24, and attack line 8, thereby purging any water remaining in attack line 8. Check valve 25 prevents water from entering brake line 26 from line 8. Fireman 6 can direct the purged water to any hot spots or fire remaining in his vicinity.

Figure 4:
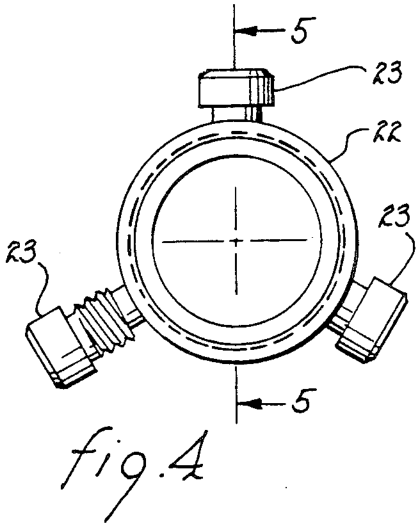
FIG. 4 is a closeup view of the air extractor of the present invention.
Figure 5:
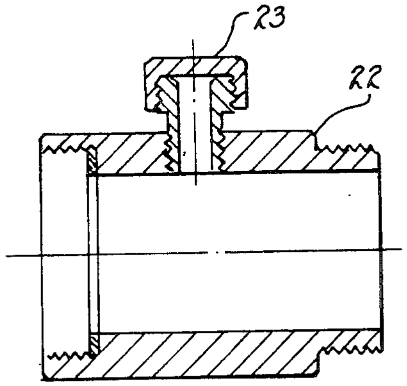
FIG. 5 is a sectional view taken on line 5—5 of FIG. 4.

As soon as the water is purged from attack line 8, fireman 6 disconnects mask hose 16 from regulator 14 and connects mask hose 16 to one of three quick-connect ports 23 of air extractor 22, shown in greater detail in FIGS. 4 and 5. At that time the fireman will begin breathing air from the truck's brake air reservoir rather than from tank 10. After air begins to flow to fireman 6, the outside fireman adjusts main valve 30 until gauge 32 indicates an air pressure of approximately 10 psig. At that pressure, three fireman can be simultaneously supported by air provided through attack line 8 to their individual mask hoses 16 connected to respective ports 23 of extractor 22. Check valve 31, located between main valve 30 and gauge 32, is a safety feature to protect the truck's brake system in the event check valve 25 fails.

Figure 2:
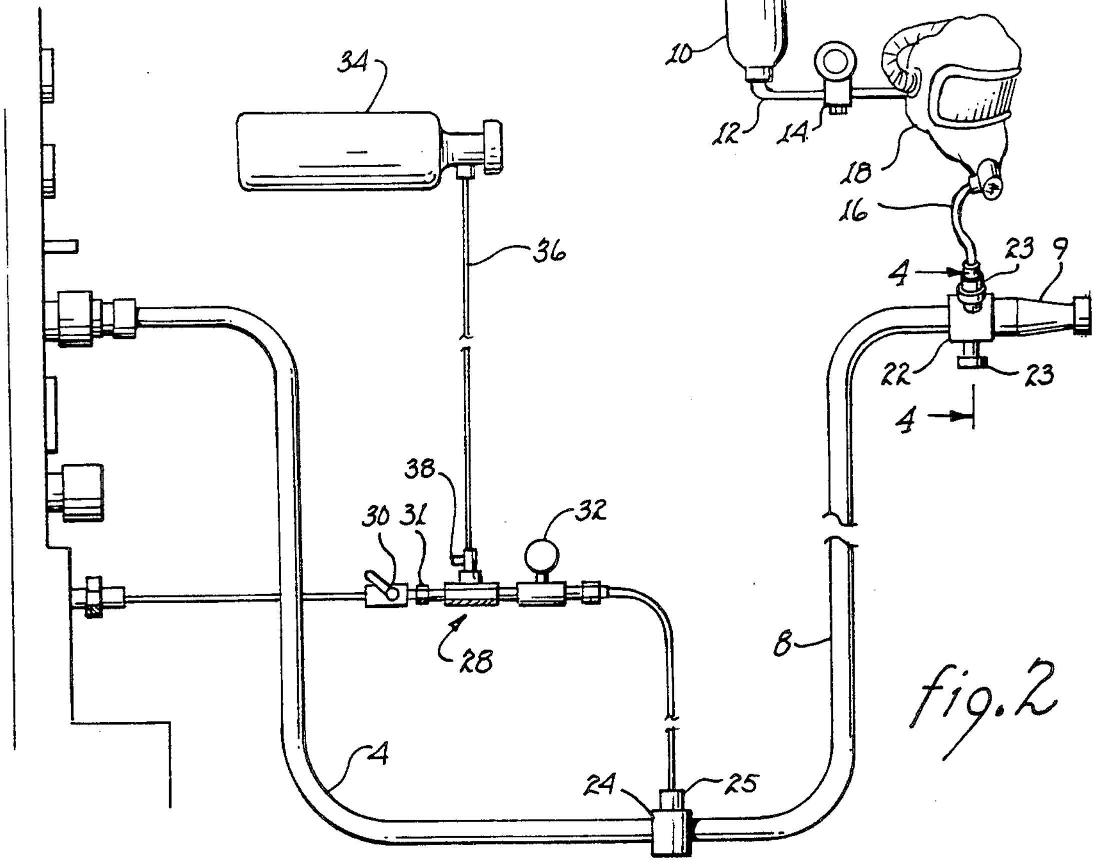
FIG. 2 is a plan view of one embodiment of the emergency air delivery system of the present invention.
Figure 3:
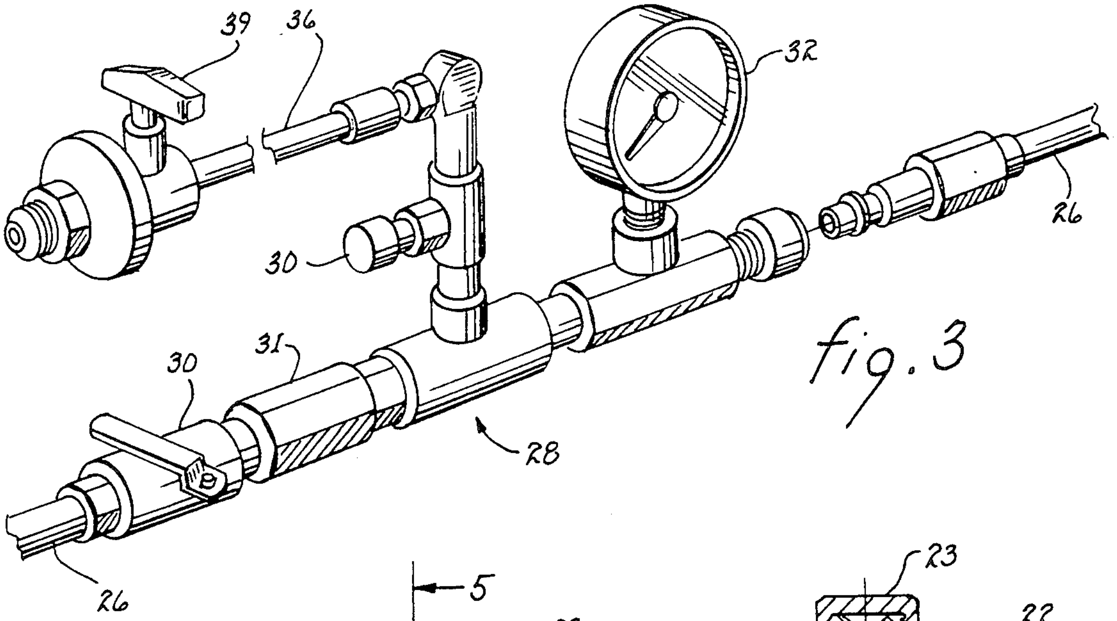
FIG. 3 is a closeup view of a pressure gauge and several valves of the embodiment illustrated in FIG. 1.

Although air from the truck's brake air system is breathable, it often has an oily aroma. The National Fire Protection Association (NFPA) Code 1500 §5-3.4 requires that breathing air supplied to fireman meet a certain quality standard not commonly achievable with brake air. Therefore, it is preferable to connect a higher quality air supply to the delivery system as soon as possible. FIG. 2 shows relief air cylinder 34 containing breathing standard quality compressed air at a pressure of approximately 2,000 psig, which is connected by means of high pressure line 36 to pressure regulator valve 38 attached to air brake line 26 upstream of gauge 32. Regulator valve 38 reduces the air pressure from 2,000 psig to approximately 300 psig, which is the maximum pressure rating of attack line 8. The outside fireman can further reduce the air pressure to approximately 8–50 psig by manipulating cylinder valve 39 located at relief cylinder 34. As an alternative to using relief air cylinders, the outside fireman can connect air brake line 26 to a cascade truck (not shown) which contains an essentially unlimited supply of high quality air in several breathing quality standard air cylinders refillable by an air compressor located on the cascade truck.

As soon as the breathing standard quality air supply is connected to brake line 26, the outside fireman closes main valve 30 to prevent high pressure air from entering and damaging the pumper truck's brake system. If the outside fireman neglects to close main valve 30, check valve 31 will prevent high pressure air from entering the brake system.

Figure 7:
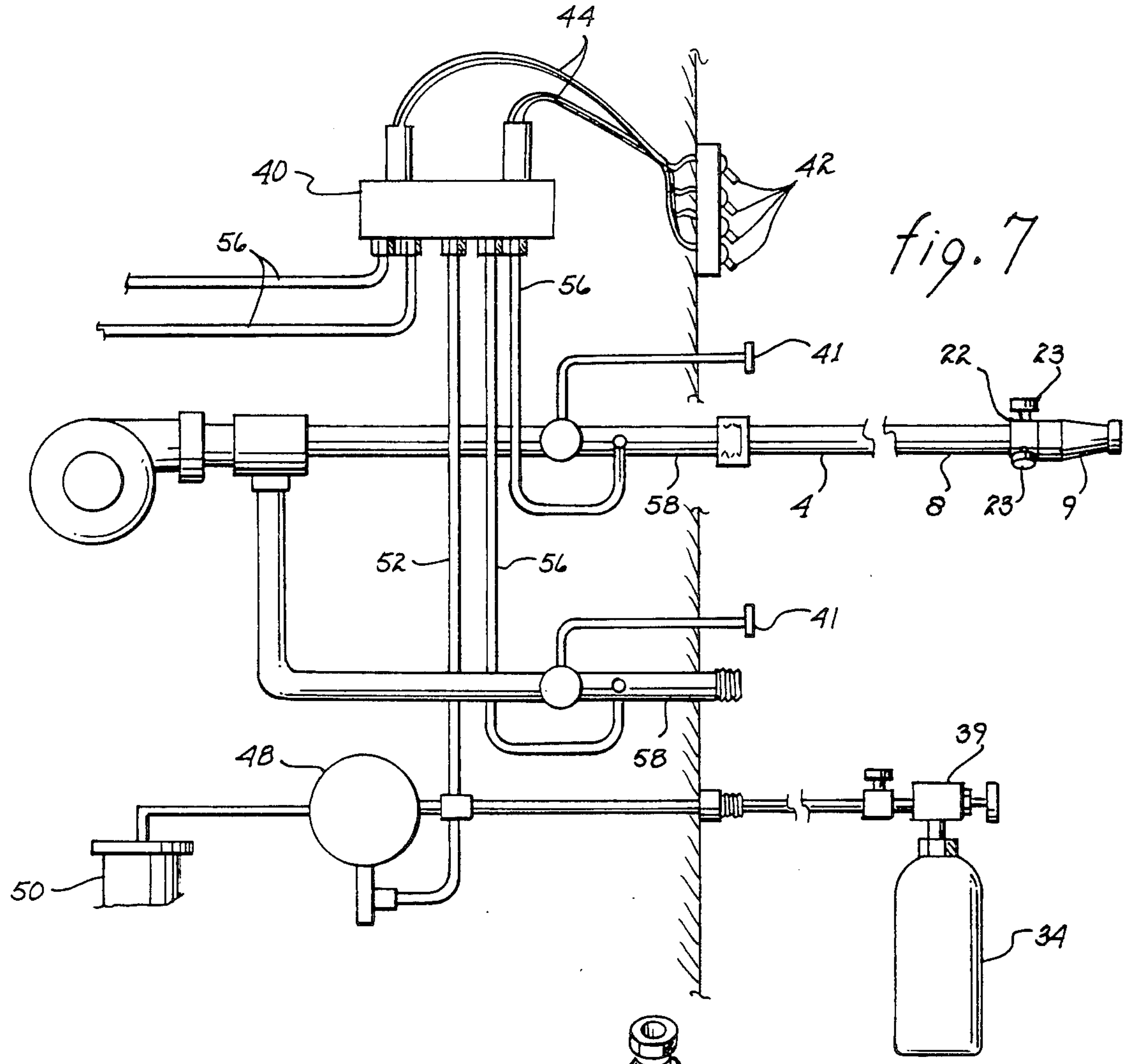
FIG. 7 is a plan view of an alternate embodiment of the present invention.
Figure 8:
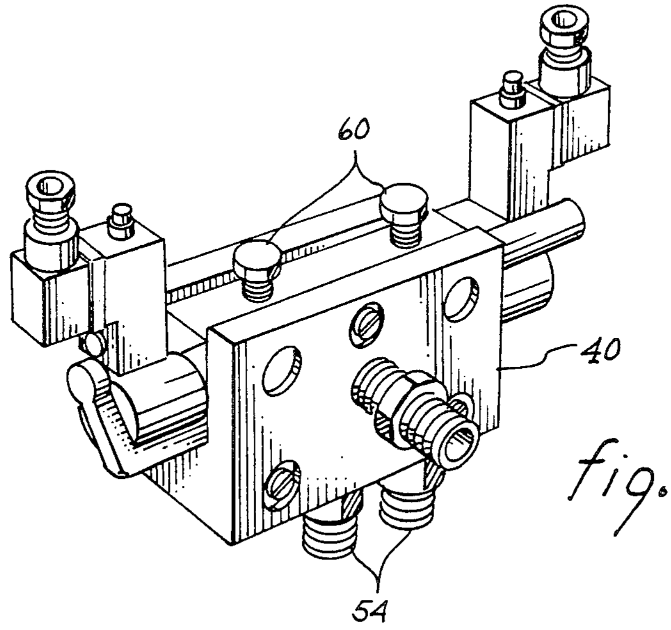
FIG. 8 is a closeup view of the air shifter module of the alternate embodiment illustrated in FIG. 7.

In the alternative embodiment shown in FIG. 7 and 8, air inductor 24, and gauge and valve assembly 28, have been replaced by air shifter module 40 located inside pumper truck 2. As with the previous embodiment, air extractor 22 is placed directly behind nozzle 9. When fireman 6 radios to outside firemen that he needs an extended supply of air, the outside fireman simply turns off the water supply to main hose 4 by manipulating one of the handles 41, and pulls switch 42 corresponding to the particular attack line 8 being used by fireman 6. When switch 42 is turned on, a signal is fed through wire 44 to air shifter module 40. In response to the signal, module 40 directs the flow of air from air brake storage tank 48, supplied by air pump 50, through air line 52 into module 40. Air exits module 40 through air outlets 54 and flows into air supply lines 56 which connect to water lines 58 leading to main hose 4. As with the previous embodiment, a breathing standard quality supply of air can be provided by connecting to air line 52 relief air cylinder 34, or a cascade system. Several parallel modules 40 can be positioned on a truck, to supply air to many main hoses at once. When switch 42 is turned off, air flow to main hose 4 ceases. Air relief valves 60 automatically open to release any air remaining inside module 40.

It is to be understood that the present invention is not limited to the particular construction and arrangement of parts disclosed and illustrated herein, but embraces all such modified forms thereof which are within the scope of the following claims.

I claim:

1. An air delivery system for emergency workers, wherein the air delivery system is adapted to be used with a water hose, the air delivery system comprising:

(a) a source of compressed air fluidically connected to the water hose for purging water from the water hose;

(b) means for adjusting the pressure of the compressed air to a pressure less than approximately 300 psig; and (c) a check valve adapted to interrupt the water flow and prevent water from entering the air hose.

2. The air delivery system of claim 1 wherein the means for supplying breathable air comprises:

(a) means for further reducing the pressure of the air in the water hose to a pressure in the range of approximately 8–50 psig; and (b) means for transferring air from the air hose to a breathing cavity of the worker.

3. An air delivery system to be used by an emergency worker wearing a compressed air cylinder connected to a breathing hose which is attached to a face mask, wherein the worker has available a water hose supplied with water from a water reservoir in a water pumping truck which has an air brake system supplying air at a pressure of approximately 100–140 psig, the air delivery system comprising:

(a) means for connecting the water hose to the air brake system after the water supply to the water hose has been shut off so that air flowing from the air brake system can purge any water remaining in the water hose;

(b) means for reducing the pressure of the air from the air brake system; and (c) means for fluidically connecting the breathing hose to the water hose so that the worker can obtain air therethrough.

4. The air delivery system of claim 3, wherein the air brake system connecting means comprises:

(a) an air inductor fluidically connected to the water hose;

(b) an air hose connected to the air brake system; and (c) a check valve connecting the inductor to the air hose, the check valve adapted to prevent water from entering the air hose.

5. The air delivery system of claim 4, wherein the pressure reducing means comprises:

(a) a main valve fluidically connected to the air hose so that the main valve can adjust air flow therethrough; and (b) a pressure gauge fluidically connected to the air hose downstream of the main valve, the gauge therefor indicating the air pressure resulting from adjustments of the main valve.

6. The air delivery system of claim 5, wherein a nozzle is attached to the end of the water hose, and wherein the breathing hose connecting means comprises a heat and fire resistant air extractor fluidically connected to the water hose and the nozzle, the extractor containing a port adapted to fluidically connect the breathing hose.

7. The air delivery system of claim 6 further comprising:

(a) a source of breathing standard quality air fluidically connected to the air hose between the main valve and the gauge;

(b) a second check valve connected to the air hose between the main valve and the quality air hose connections, the second check valve adapted to prevent quality air from entering the brake system; and (c) means for adjusting the pressure of the quality air prior to its entrance into the air hose to a pressure less than approximately 300 psig.

8. The air delivery system of claim 7 wherein the source of quality air is a compressed air cylinder connected to the air hose by a high pressure line and wherein the quality air pressure adjusting means is a pressure relief valve.

9. A method for supplying air through a water hose to an emergency worker, the method comprising the steps of:

(a) connecting to the water hose a supply of air having a pressure of less than about 300 psig;

(b) interrupting water flow to the water hose;

(c) flowing the air through the water hose, thereby purging water from the water hose;

(d) reducing the air pressure to approximately 8–50 psig; and (e) transferring air from the water hose to a breathing cavity of the worker.

10. The method of claim 9 wherein a nozzle is attached to the end of the water hose adjacent to the worker; wherein the step of transferring air includes fluidically connecting a heat and fire resistant extractor to the water hose and the nozzle, the extractor containing a port; fluidically connecting to the port a breathing hose adapted to supply air to a breathing cavity of the worker; and wherein the step of interrupting water flow includes fluidically connecting a check valve between the water hose and the air hose, the check valve adapted to prevent water from entering the air hose.

11. A method for supplying air to an emergency worker wearing a compressed air cylinder connected to a breathing hose which is attached to a face mask, wherein the worker has available a water hose supplied with water from a water reservoir in a water pumping truck which has an air brake system supplying air at a pressure of approximately 100–140 psig, the lg method comprising the steps of:

(a) connecting the water hose to the air brake system after the water supply to the water hose has been shut off so that air flowing from the air brake system can purge any water remaining in the water hose;

(b) reducing the pressure of the air from the air brake system to approximately 8–50 psig; and (c) fluidically connecting the breathing hose to the water hose so that the worker can obtain air therethrough.

12. The method of claim 11, wherein step (a) includes:

(a) fluidically connecting an air inductor to the water hose;

(b) connecting an air hose to the air brake system; and (c) connecting a check valve between the inductor and the air hose, the check valve adapted to prevent water from entering the air hose.

13. The method of claim 12, wherein the pressure reducing step includes:

(a) fluidically connecting a main valve to the air hose so that the main valve can adjust air flow therethrough; and (b) fluidically connecting a pressure gauge to the air hose downstream of the main valve, the gauge therefor indicating the air pressure resulting from adjustments of the main valve.

14. The method of claim 13, wherein a nozzle is attached to the end of the water hose and wherein the step of fluidically connected the breathing hose to the water hose includes fluidically connecting a heat and fire resistant air extractor to the water hose and the nozzle, the extractor containing a port adapted to fluidically connect the breathing hose.

15. The method of claim 14 further comprising the steps of:

(a) fluidically connecting a source of breathing standard quality air to the air hose between the main valve and the gauge;

(b) connecting a second check valve to the air hose between the main valve and the quality air hose connections, the second check valve adapted to prevent quality air from entering the brake system; and (c) adjusting the pressure of the quality air prior to its entrance into the air hose to a pressure less than approximately 300 psig.

* * * * *